United States Patent
Li et al.

(10) Patent No.: US 8,851,747 B2
(45) Date of Patent: *Oct. 7, 2014

(54) THERMAL CONDUCTIVITY MEASUREMENT APPARATUS FOR ONE-DIMENSIONAL MATERIAL

(71) Applicants: Tsinghua University, Beijing (CN); Hon Hai Precision Industry Co., Ltd., New Taipei (TW)

(72) Inventors: Qing-Wei Li, Beijing (CN); Chang-Hong Liu, Beijing (CN); Shou-Shan Fan, Beijing (CN)

(73) Assignees: Tsinghua University, Beijing (CN); Hon Hai Precision Industry Co., Ltd., New Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/869,965

(22) Filed: Apr. 25, 2013

(65) Prior Publication Data

US 2013/0235900 A1  Sep. 12, 2013

Related U.S. Application Data

(63) Continuation of application No. 12/620,073, filed on Nov. 17, 2009, now Pat. No. 8,459,866.

(30) Foreign Application Priority Data

May 8, 2009  (CN) .......................... 2009 1 01074016

(51) Int. Cl.
  *G01K 1/08* (2006.01)
  *G01N 25/18* (2006.01)

(52) U.S. Cl.
  CPC ..................................... *G01N 25/18* (2013.01)
  USPC ............................................ 374/44; 374/141

(58) Field of Classification Search
  USPC ..................................................... 374/44, 141
  See application file for complete search history.

(56) References Cited

U.S. PATENT DOCUMENTS 3,266,290 A * 8/1966 Gottfried ......................... 374/44
8,459,866 B2 * 6/2013 Li et al. ........................... 374/44

OTHER PUBLICATIONS

Li et al., "Measuring the thermal conductivity of individual carbon nanotubes by the Raman shift method" Nanotechnology 20 (Mar. 18, 2009).*
Zheng et al., Utralong single-wall carbon nanotubes, Nature material, vol. 3, 2004, p. 673-676.
Hong et al., Quasi-continuous Growth of Ultralong Carbon Nanotube Arrays, J. Am. Chem. Soc, vol. 127, No. 44, 2005, p. 15336-15337.

* cited by examiner

*Primary Examiner* — Mirellys Jagan
(74) *Attorney, Agent, or Firm* — Novak Druce Connolly Bove + Quigg LLP

(57) ABSTRACT

A thermal conductivity measurement apparatus for measuring a thermal conductivity of a one-dimensional material includes a substrate, a vacuum chamber receiving the substrate and four spaced electrodes. The one-dimensional material spans across the four spaced electrodes. A middle part of the one-dimensional material, located between the second and third electrodes, is suspended.

10 Claims, 3 Drawing Sheets

THERMAL CONDUCTIVITY MEASUREMENT APPARATUS FOR ONE-DIMENSIONAL MATERIAL

This application is a continuation of U.S. patent application Ser. No. 12/620,073, filed on Nov. 17, 2009, entitled, "THERMAL CONDUCTIVITY MEASUREMENT APPARATUS FOR ONE-DIMENSIONAL MATERIAL AND MEASUREMENT METHOD," which claims all benefits accruing under 35 U.S.C. §119 from China Patent Application No. 200910107401.6 filed on May 8, 2009 in the China Intellectual Property Office. The disclosures of the above-identified applications are incorporated herein by reference.

BACKGROUND

1. Technical Field

The present disclosure relates to measurement apparatuses and measurement methods, and particularly to a thermal conductivity measurement apparatus for one-dimensional material and a measurement method using the same.

2. Discussion of Related Art

Thermal conductivity is an important parameter which reflects the thermal properties of a material. Selecting a suitable material is an important issue in heat conduction technology. Therefore, how to measure the exact thermal conductivity of a material is important for the application of the material.

When the material that needs to be measured is a one-dimensional nano-material, such as nanowires or carbon nanotubes, it is more difficult to measure the thermal conductivity. One reason is, that measuring instruments are large compared to the areas of nano-materials to be measured and so immediately affect the temperature of the material when contact is made during measurement.

BRIEF DESCRIPTION OF THE DRAWINGS

Many aspects of the embodiments can be better understood with references to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
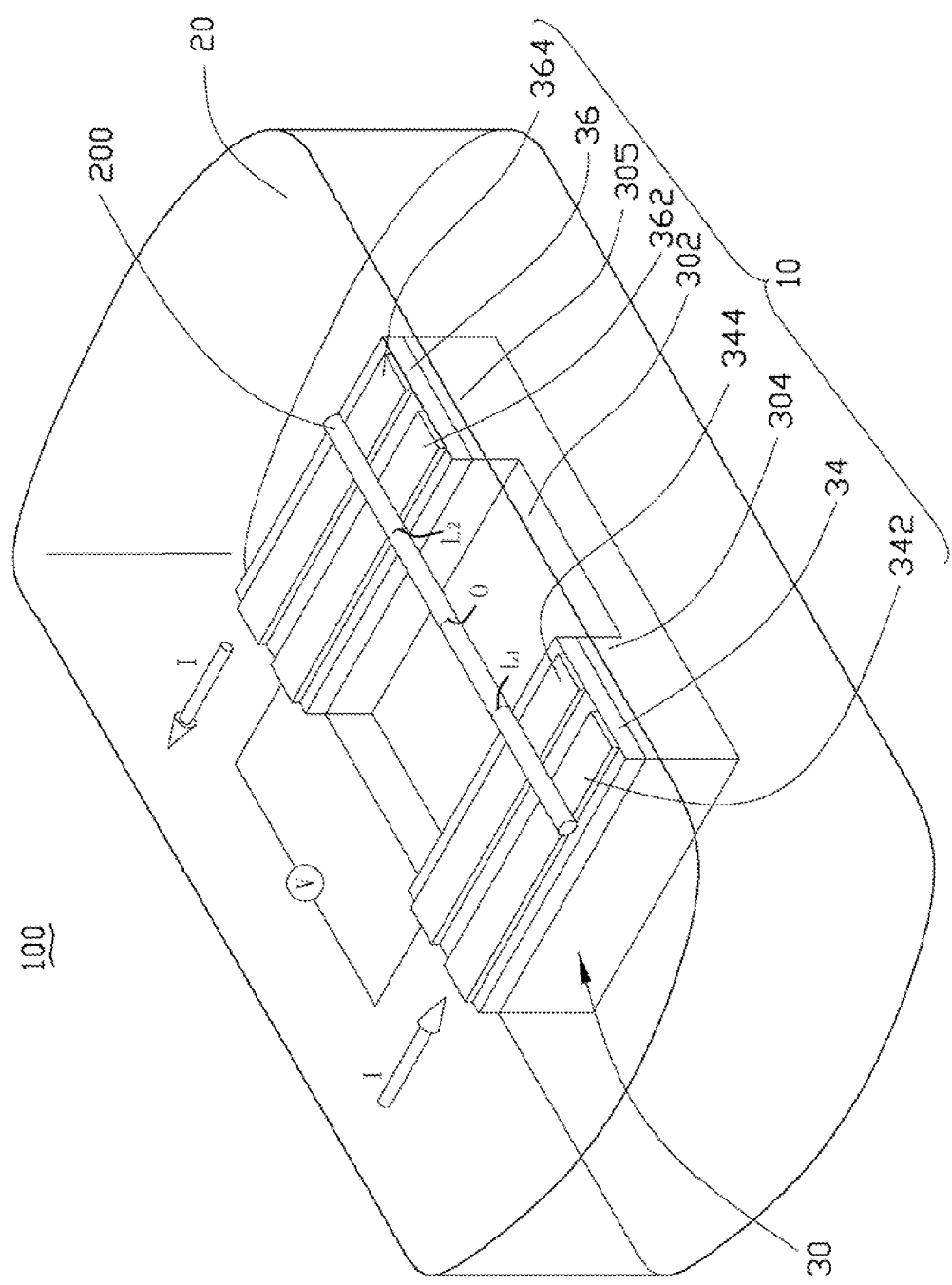
FIG. 1 illustrates a structural schematic view of an embodiment of a thermal conductivity measurement apparatus.

Referring to FIG. 1, an embodiment of a thermal conductivity measurement apparatus 100 is shown. The thermal conductivity measurement apparatus 100 is used to measure a thermal conductivity ω of an object 200. In one embodiment, the object 200 is a one-dimensional material whose characteristic band frequency value of Raman-spectra varies linearly with its temperature. The one-dimensional material can be a one-dimensional nanometer sized material or one-dimensional micrometer sized material. The one-dimensional nanometer material can comprise nanotubes, nano-rods, nanowires, nanofibers, nano-tips, nano-pillars, nano-ribbons, for example.

The thermal conductivity measurement apparatus 100 comprises a support device 10 for supporting the object 200 and a vacuum chamber 20. The support device 10 is located in the vacuum chamber 20. The vacuum chamber 20 can be made of quartz glass. Vacuum degree of the vacuum chamber 20 is approximately $10^{-4}$ Torr.

The support device 10 includes a substrate 30, a first insulated layer 34, a second insulated layer 36, a first electrode 342, a second electrode 344, a third electrode 362, and a fourth electrode 364.

The substrate 30 defines a groove 302 at a top surface thereof such that a first step 304 and a second step 305 are correspondingly formed at two flanks of the groove 302. The object 200 is mounted on the first and second steps 304, 305 and is suspended over the groove 302. The groove 302 is located at a center of the substrate 30. The first insulated layer 34 is formed on a top surface of the first step 304. The second insulated layer 36 is formed on a top surface of the second step 305. The material of the insulated layers 34, 36 is a dielectric.

The first electrode 342 and the second electrode 344 are mounted on a top surface of the first insulated layer 34 and spaced apart from each other. The third electrode 362 and the fourth electrode 364 are arranged on a top surface of the second insulated layer 36 and are spaced apart from each other. The four electrodes 342, 344, 362, and 364 are parallel to each other. The four electrodes 342, 344, 362 and 364 can be made of molybdenum, platinum, or nickel. In one embodiment, the four electrodes 342, 344, 362, and 364 comprises of molybdenum. The first electrode 342 and the fourth electrode 364 are connected in series via an ammeter (not shown) and an electrical source (not shown). The second electrode 344 and the third electrode 362 are connected via a voltmeter V.

The object 200 spans across and is electrically connected to the four electrodes 342, 344, 362, and 364. In detail, a first end of the object 200 is mounted on the first electrode 342 and the second electrode 344. A second end of the object 200 is mounted on the third electrode 362 and the fourth electrode 364. The remaining portion of the object 200 located between the second electrode 344 and the third electrode 362 is suspended and can be acted as a suspended part. The object 200 is oriented to be perpendicular to the four electrodes 342, 344, 362, and 364. By such arrangement, a current flows into the object 200 through the first electrode 342 and flows out the object 200 through the fourth electrode 364.

Two points where the second electrode 344 and the third electrode 362 contact with the object 200 define two opposite ends of the suspended part. Constructing a coordinate system for the suspended part, a center point O is the middle point and two points $L_1$, $L_2$ are the two opposite ends points of the suspended part.

The thermal conductivity ω of the object 200 can be calculated as:

$$\omega = \frac{P\Delta L}{S\Delta T}.$$

Where P is thermal power (heat flow) through the suspended part of the object 200 along the axial direction thereof; ΔL is a length of the suspended part of the object 200, which means the distance between the two points $L_1$, $L_2$; S is an area of the cross section of the object 200; ΔT is a temperature difference between temperatures of the center point O and one of the two points $L_1$, $L_2$.

The thermal conductivity ω of the object 200 is measured by using the thermal conductivity measurement apparatus 100. An example using a single wall carbon nanotube (SWCNT) as the object 200 is used to explain how to measure the thermal conductivity ω.

Measurement for L

L is a distance between the second electrode 344 and the third electrode 362 of the support device 10. L can be measured by using a scanning electron microscope. When the object 200 is perpendicular with the four electrodes, the L is equal to the distance between the second electrode and the third electrode. L can be measured by using a scanning electron microscope image of the support device 10 and the scale of the image. In one embodiment, L is 30 micrometers (μm).

Measurement for S

Shape of the cross section of the object 200 is an annulus. An outer radius R and a wall thickness b of the annulus are measured. The outer radius R of the annulus can be measured by using an atomic force microscope image of the object 200 and the scale of the image. In one embodiment, the outer radius R of the annulus is 1.8 nanometers (nm). The wall thickness b of the annulus is 0.34 nm and b is a constant for the object 200. Therefore, S is calculated as $S=\pi(2R-b)b=1.1084\pi$ square nanometers ($nm^2$).

Measurement for P

P relates to total heat which is equal to the summation of heat convection from the object 200 to ambient air, infrared radiation heat, and heat flowing through suspended part of the object 200 along the axial direction thereof. When a current I flows through the object 200, the object 200 is heated by the current I and generates the total heat. Due to the high vacuum degree of the vacuum chamber 20, heat convection from the object 200 to ambient air may be neglected. The infrared radiation heat is also a very small portion of the total heat and can also be neglected. Therefore, when the object 200 is heated by the current I, the total heat is taken to equal the heat flowing through the object 200 along an axial direction of the object 200. The total thermal power is equal to the total heat divided by time. The thermal power P is equal to the heat flowing through the object 200 along an axial direction of the object 200 divided by time. Therefore, the total thermal power is equal to the thermal power P flowing through the object 200 along an axial direction of the object 200. The total thermal power $P_{total}$ can be calculated as $P_{total}=UI$; therefore, the thermal power P flowing through the object 200 is equal to $P_{total}$ and can also be calculated as $P=UI$. U is amount of voltage across the suspended part of the object 200, and I represent the current flowing through the object 200.

An embodiment for obtaining U and I includes the following steps:

(A) placing the object 200 on the surfaces of the four electrodes 342, 344, 362, and 364 of the support device 10;

(B) placing the object 200 and the support device 10 in the vacuum chamber 20;

(C) applying I through the object 200, and the object 200 is heated by the current and reaches heat balance; the heat steadily conducts from the center point O to the two ends $L_1$, $L_2$ of the object 200, because the temperature at the center point O of the suspended object 220 is higher than that of the two points $L_1$, $L_2$ which are contacted with the substrate 30;

(D) reading the ammeter and obtaining the value of I; for the tested SWCNT, I is 0.298 microampere (μA); and (E) reading the voltmeter and obtaining the value of U; for the tested SWCNT, U is 1.175 volts (V).

Therefore, $P=UI=3.5\times10^{-7}$ Watts (W).

In one embodiment, step (A) includes the following steps:

Step A1, providing a growing substrate on a lateral side of the first electrode 342 or the fourth electrode 362 and placing the growing substrate and the support device 10 in a growing chamber.

Step A2, providing a ferric trichloride solution of concentration about $10^{-6}$-$10^{-5}$ mol/L. In one embodiment, the ferric trichloride solution of concentration is $3\times10^{-6}$ mol/L. The ferric trichloride solution works as the catalyst precursor. The concentration of the ferric trichloride solution is low enough to ensure an individual SWCNT is formed on the surfaces of the growing surface.

Step A3, heating up the ferric trichloride solution to 950° C. and flowing mixed gas comprising $H_2$ and He into the growing chamber at a rate of 60-200 cubic centimeter per minute ($cm^3$/min.);

Step A4, adding carbon source gas into the growing chamber as the carbon source gas and growing an individual SWCNT on the surfaces of the growing surface. In one embodiment, the carbon source gas is $H_2$ and $CH_4$. When an individual SWCNT is grown, the SWCNT falls on the surfaces of the four electrodes 342, 344, 362, and 364 by controlling the direction of the carbon source gas. The grown SWCNT has no support so that it falls down across the surfaces of the four electrodes easily and perpendicular with the four electrodes by the force of the flowing carbon source gas.

The SWCNT is not needed to be grown in a vacuum. Alternatively, an individual SWCNT can be placed on the surfaces of the four electrodes 342, 344, 362 and 364 of the support device 10 directly.

Measurement for ΔT

ΔT is obtained by using a characteristic band frequency value difference ΔC between the center point O and one of the two points $L_1$, $L_2$ and a slope K of a curve representing the temperature dependence of the characteristic band frequency value of Raman-spectra of the object 200. ΔT can be calculated as: $\Delta T=K\Delta C$. The characteristic band frequency value of the Raman-spectra is different when the object 200 is made of different material. For a SWCNT, the characteristic band frequency value of Raman-spectra is G band frequency. ΔG is the G band frequency value difference between the center point O and one of the two points $L_1$, $L_2$ of the suspended part of the object 200. The G band is the highest band in the Raman-spectra.

An embodiment for obtaining ΔT includes the following steps:

Step 21, obtaining a plurality of the G band frequency values of Raman-spectra of the object 200 at different predetermined temperatures after mounting the object 200 on the four electrodes 342, 344, 362, and 364 but before the current flows into the one-dimensional material and getting a plurality of data corresponding to the different predetermined temperatures.

The support device 10 may be placed in a temperature controlling apparatus. The temperature controlling apparatus can control the temperature of the support device 10 and the object 200. The object 200 is placed in the support device 10 and has no electricity flowing through it. The temperature of the temperature controlling apparatus can be predetermined. The G band frequency value of Raman-spectra of the object 200 is measured at the predetermined temperature of the temperature controlling apparatus.

Figure 2:
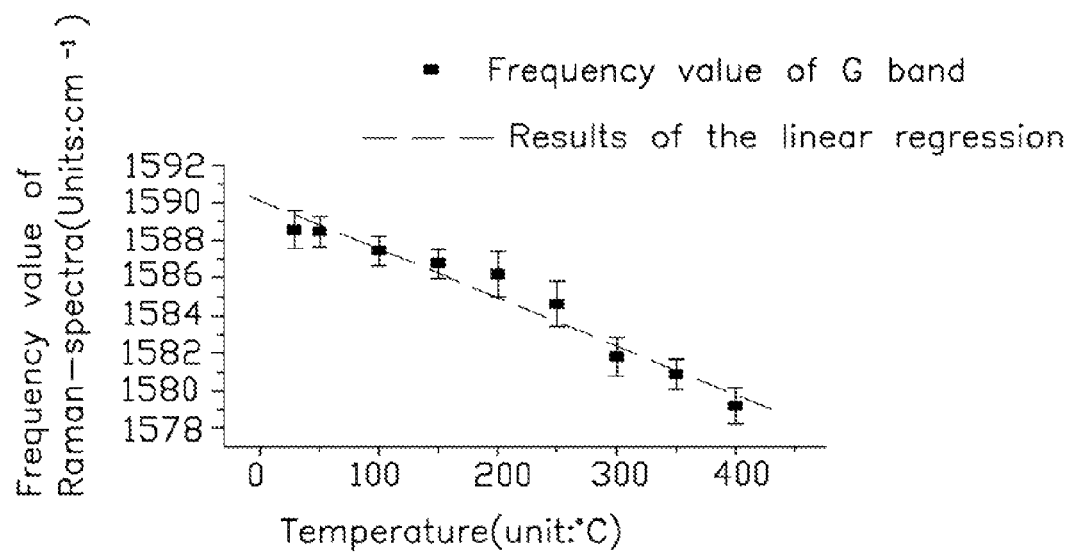
FIG. 2 illustrates a curve representing temperature dependence of the G band frequency value of an object.

Step 22, fitting the plurality of data to a curve representing the temperature dependence of the G band frequency value of Raman-spectra. The method for fitting a plurality of data can be with the use of linear regression, non-linear regression, or with a spline function. In one embodiment, the data is fit by linear regression and a broken line is obtained as shown in FIG. 2. The broken line is the curve representing the temperature dependence of the G band frequency value of Raman-spectra of the object 200.

Step 23, calculating a slope K of the curve representing the temperature dependence of the G band frequency value of Raman-spectra. In one embodiment, referring to FIG. 2, the slope K of the broken line is $-0.0257$ cm$^{-1}$/K.

Step 24, comparing the G band frequency value of Raman-spectra at the center point O to the G band frequency value of Raman-spectra of one of the two points $L_1$, $L_2$ to obtain $\Delta G$. The G band frequency value of Raman-spectra at the center point O of the object 200 is defined as $G_1$. The G band frequency value of Raman-spectra of one of the two points $L_1$, $L_2$ is defined as $G_2$.

$G_1$ and $G_2$ are measured by a Roman spectrometer. A Raman-laser emitted by the Roman spectrometer is focused at the center point O and one of the two points $L_1$, $L_2$ of the object 200 to obtain two Raman-spectras thereof. Because the resolution ability of the Raman-laser can reach to 1 μm so that each point of suspended part of the object 200 having a length of 30-micrometer can be accurately measured. The wavelength of the Raman-laser employed is 514.5 nm. When a current I flows through the object 200, the object 200 is heated by the current and reaches heat balance. After reaching heat balance, there is a steady temperature distribution along the object 200 and $G_1$ and $G_2$ of the object 200 can be measured subsequently. The number of the measurement times that the center point O and one of the two points $L_1$, $L_2$ of the object 200 are measured can exceed three times. A final result is an average of the measuring results.

Figure 3:
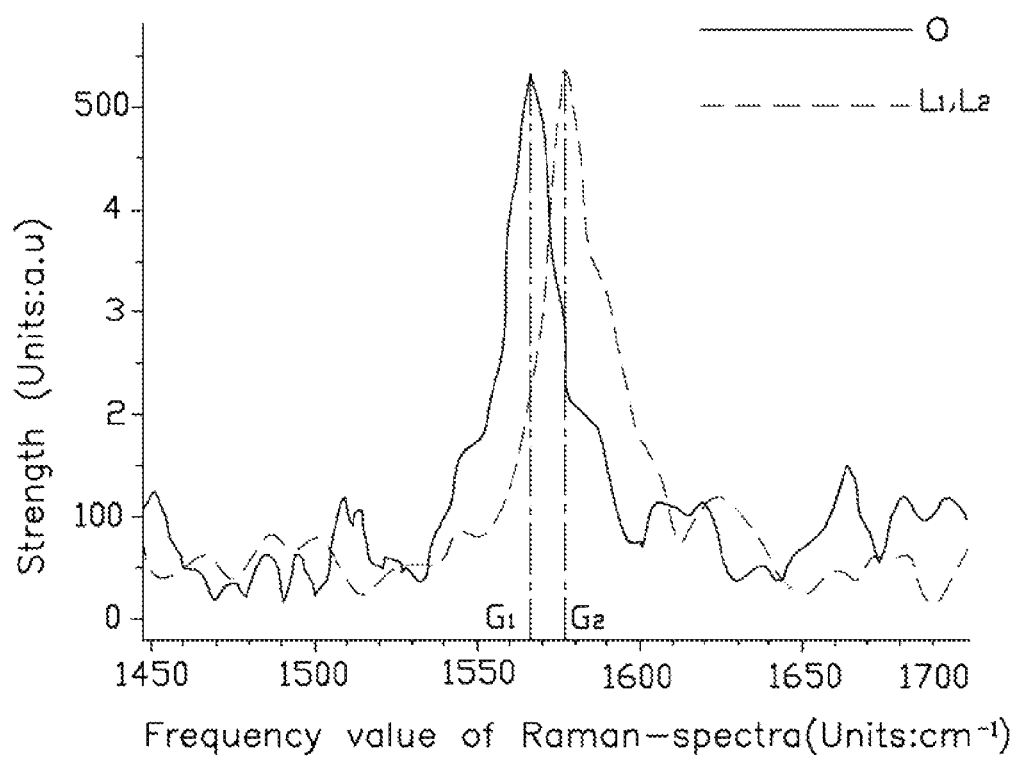
FIG. 3 shows a Raman-spectra in a center point O and one of two points $L_1$, $L_2$ of the suspended part of an object.

Referring to FIG. 3, $G_1$ is 1567.6 centimeters$^{-1}$(cm$^{-1}$), $G_2$ is 1577.7 cm$^{-1}$. Therefore, $\Delta G = G_1 - G_2 = 1567.6$ cm$^{-1} - 1577.7$ cm$^{-1} = -10.1$ cm$^{-1}$.

Step 25, substitute the value of the $\Delta G$ and K into the formula $\Delta T = K \Delta G$. Thus, $\Delta T$ is calculated as $\Delta T = (-10.1$ cm$^{-1})(-0.0257$ cm$^1$/K$) = 393$K.

At last, for SWCNT, $$\omega = \frac{P \Delta L}{S \Delta T} = \frac{UI \Delta L}{\pi(2R-b)b \Delta G K}..$$

Where P=UI=$3.5 \times 10^{-7}$ W, L=30 μm, S=$\pi(2R-b)b = 1.1084\pi$ and $\Delta T = 393$K. Then, $$\omega \approx 2400 \text{ W/mK}$$

Therefore, the thermal conductivity ω of SWCNT is 2400 W/mK.

In conclusion, the present disclosure relates to a non-contact measurement apparatus and measurement method so as to avoid the object 200 contact with elements whose heat capacity is large. Therefore, the temperature of the object 200 is steady and the result of the measurement is more exact.

Depending on the embodiments, certain of the steps described may be removed, others may be added, and the sequence of steps may be altered. It is also to be understood that the description and the claims drawn to a method may include some indication in reference to certain steps. However, the indication used is only to be viewed for identification purposes and not as a suggestion as to an order for the steps.

It is to be understood, however, that even though numerous characteristics and advantages of the present embodiments have been set forth in the foregoing description, together with details of the structures and functions of the embodiments, the disclosure is illustrative only, and changes may be made in detail, especially in matters of shape, size, and arrangement of parts within the principles of the disclosure.

What is claimed is:

1. A thermal conductivity measurement apparatus, the thermal conductivity measurement apparatus comprising:
   a vacuum chamber;
   a substrate located in the vacuum chamber and defining a groove;
   a first step and a second step located at two flanks of the groove; and
   a first electrode, a second electrode, a third electrode, and a fourth electrode spaced apart from each other; wherein the first electrode and the second electrode are located on the first step, and the third electrode and the fourth electrode are located on the second step; the first electrode, the second electrode, the third electrode, and the fourth electrode are configured to support a one-dimensional material; and the one-dimensional material is suspended above the groove.

2. The thermal conductivity measurement apparatus of claim 1, further comprising: a first insulated layer located on the first step; a second insulated layer located on the second step; and the first electrode and the second electrode are located on the first insulated layer, and the third electrode and the fourth electrode are located on the second insulated layer.

3. The thermal conductivity measurement apparatus of claim 1, wherein the groove is defined at a center of the substrate.

4. The thermal conductivity measurement apparatus of claim 1, wherein the first electrode, the second electrode, the third electrode, and the fourth electrode are electrically connected to the one-dimensional material; the first electrode and the fourth electrode are coupled to an ammeter and an electrical source; and the second electrode and the third electrode are electrically connected with a voltmeter.

5. The thermal conductivity measurement apparatus of claim 1, wherein the first electrode, the second electrode, the third electrode, and the fourth electrode are parallel to each other.

6. The thermal conductivity measurement apparatus of claim 5, wherein the one-dimensional material is oriented to be perpendicular to the first electrode, the second electrode, the third electrode, and the fourth electrode.

7. The thermal conductivity measurement apparatus of claim 1, wherein the one-dimensional material is a one-dimensional nanometer sized material or one dimensional micrometer sized material.

8. The thermal conductivity measurement apparatus of claim 7, wherein the one-dimensional material comprises nanotubes, nanorods, nanowires, nanofibers, nanotips, nanopillars, or nanoribbons.

9. The thermal conductivity measurement apparatus of claim 1, wherein a thermal conductivity ω of the one-dimensional material is calculated as:

$$\omega = \frac{P \Delta L}{S \Delta T},$$

where P is thermal power through a suspended part of the one dimensional nanostructure along an axial direction thereof; $\Delta L$ is a length of the suspended part of the one-dimensional material which means a distance between two points $L_1$, $L_2$; S is an area of a cross section of the one-dimensional material; and $\Delta T$ is a temperature difference between temperatures of a center point O and one of the two points $L_1$, $L_2$.

10. The thermal conductivity measurement apparatus of claim 9, further comprising a Raman spectrometer, and a Raman-laser emitted by the Raman spectrometer is focused at the center point O and one of the two points $L_1$, $L_2$ of the one-dimensional material.

* * * * *